(12) United States Patent
Rogozinski

(10) Patent No.: US 6,664,254 B1
(45) Date of Patent: Dec. 16, 2003

(54) ODOR-ELIMINATING COMPOSITION

(75) Inventor: Wallace Rogozinski, Rainbow Lake Club, 1087 Lakeview Ter., Azusa, CA (US) 91702

(73) Assignee: Wallace Rogozinski, San Dimas, CA (US)

(*) Notice: Subject to any disclaimer, the term of this patent is extended or adjusted under 35 U.S.C. 154(b) by 68 days.

(21) Appl. No.: 09/504,963

(22) Filed: Feb. 16, 2000

(51) Int. Cl.$^7$ ............................................. A61K 31/535
(52) U.S. Cl. ................. 514/231.2; 514/237.8; 514/238.8
(58) Field of Search ................ 514/231.2, 237.8, 514/238.8

(56) References Cited

U.S. PATENT DOCUMENTS 4,851,214 A * 7/1989 Walters et al. ............... 424/65
5,676,937 A * 10/1997 Eigen et al. ................ 424/65

FOREIGN PATENT DOCUMENTS

EP        288 633       * 11/1988

OTHER PUBLICATIONS

Belle–Aire, New Fragrance Material for Personal Care Products, Drug & Cosmetic Industry, Dec. '96, pp. 48,49, 1996.*

* cited by examiner

*Primary Examiner*—Alton N. Pryor
(74) *Attorney, Agent, or Firm*—Finnegan, Henderson, Farabow, Garrett & Dunner LLP

(57) ABSTRACT

The present invention relates to odor eliminating compositions, including air fresheners, and methods of eliminating odors. The inventive compositions comprise soyaethyl morpholinium ethosulfate, benzethonium chloride, and Ordenone®.

8 Claims, No Drawings

ODOR-ELIMINATING COMPOSITION

FIELD OF THE INVENTION

This invention relates to odor-eliminating compositions, including air fresheners, and methods of eliminating odors. The inventive compositions comprise soyaethyl morpholinium ethosulfate, benzethonium chloride, and Ordenone®.

1. Background of the Invention

Most air fresheners and odor eliminators rely on perfume and fragrances to counteract the foul smelling rancidity associated with the by-products of biological and organic decomposition. Perfumes contained in air fresheners provide only very limited odor control, as they simply afford only short term masking of the offensive odors. This masking is quickly followed by characteristic "odor rebound."

The distinct chemical components that constitute disagreeable smells of decaying organic matter are typically represented as low molecular weight fatty acids, mercaptans, amines, indols, ammonia, and hydrogen sulfide, on which fragrances and perfumes have little or no long lasting counter effect.

The present invention exhibits exceptional odor-nullifying properties, principally through the combined action of soyaethyl morpholinium ethosulfate, benzethonium chloride and Ordenone®. Ordenone® is a registered trademark of Belle-Aire Fragrances, Inc., Mundelein, Ill., for a highly concentrated deodorizing agent. This deodorizing agent is a proprietary synergistic composition comprising a number of active ingredients combined to provide a single deodorizer fragrance composition. This composition is water-based and features semi-rigid, concave molecular structures. The theoretical internal cavities of these concave molecular structures have the unique ability to "capture" odor-causing molecules.

Soyaethyl morpholinium ethosulfate functions by both complexing and neutralizing certain odiferous organic molecules. This has the effect of reducing their concentration in the vapor phase. Benzethonium chloride is effective against the bacteria and other microorganisms that are responsible for the decomposition of organic matter. Ordenone® has the ability to capture malodorous molecules and inactivate them in its unusual concave molecular core, which is created during the exothermic reaction synthesis segment of the manufacturing process.

2. Description of the Related Art

U.S. Pat. No. 2,634,229 to de Wet relates to the use of certain quaternary ammonium compounds as deodorants for sanitary napkins. Benzethonium chloride (diisobutyl phenoxy ethoxyethyldimethylbenzyl ammonium chloride) is disclosed as one of several suitable quaternary ammonium compounds (Col. 2, line 17).

U.S. Pat. No. 3,198,251 to Shore relates to water-dispersible or water-soluble deodorant preparations containing a water-soluble benzethonium quaternary salt, which functions as a deodorizing agent, and a water-soluble nitrate. Benzethonium chloride is specifically disclosed (Col. 1, line 64).

U.S. Pat. No. 5,739,168 to Hioki et al. is directed to germicidal disinfectant detergent compositions comprising a cationic germicide, a metal chelating agent, and a (Col. 2, line 29). EDTA is disclosed as a suitable chelating agent (Col. 2, line 49). Polyoxyethylene sorbitan fatty acid esters are identified as suitable surfactants (Col. 3, lines 4647).

U.S. Pat. No. 4,851,214 to Walters et al. discloses the use of soyaethyl morpholinium ethosulfate as a deodorizing agent in various formulations. This patent generally teaches aerosol formulations containing soyaethyl morpholinium ethosulfate in combination with "biocides and/or fragrances" (Col. 2, line 43).

Similarly, U.S. Pat. No. 5,180,749 to Cusack et al. discloses the use of soyaethyl morpholinium ethosulfate as a deodorizing agent in aqueous ethanolic antimicrobial formulations. Such compositions are used for disinfecting hard, nonporous surfaces.

SUMMARY OF THE INVENTION

The purpose of this invention is to eliminate or neutralize airborne odors through the chemical interaction of soyaethyl morpholinium ethosulfate, benzethonium chloride, and Ordenone , with the gaseous fraction of the odor-causing compounds, to form an insoluble association complex.

DESCRIPTION OF THE INVENTION

The active odor-eliminating compounds may be combined with volatile and non-volatile solvents, solubilizing agents, chemical carriers, chelators, fragrances, and colorants to form a liquid that can be atomized, either by a mechanical spraying device or a compressed gas aerosol apparatus, into a fine mist spray.

One embodiment of the present invention relates to an odor-eliminating composition comprising Ordenone®, soyaethyl morpholinium ethosulfate, and benzethonium chloride.

Another embodiment of the present invention relates to a method for eliminating or neutralizing odor, comprising applying to a locus in need of such elimination or neutralization an effective amount of a composition comprising Ordenone®, soyaethyl morpholinium ethosulfate, and benzethonium chloride.

The following represents approximate ratios of ingredients for the compositions according to the invention:

| | |
|---|---|
| Ordenone ® | 0.1–5% |
| Soyaethyl morpholinium ethosulfate | 0.1–5% |
| Benzethonium chloride | 0.1–3% |
| EDTA | 0.05–1% |
| Colorant | 0.01–0.5% |
| Polysorbate | 3–15% |
| Triethylene glycol | 1–12% |
| Fragrance | 0.5–10% |
| Deionized water | 25–60% |
| Denatured Alcohol | 5–45% |

All percentages are approximate, and are percent by weight.

With regard to the fragrance component, the key to the odor-eliminating compositions according to the invention is not the fragrance but instead is the interaction of the three active ingredients. However, it has been found that the compositions according to the invention may contain a fragrance composition which imparts a unique "smell" to the odor-eliminating composition. This fragrance composition comprises two different proprietary fragrances purchased from Elias Fragrances, Inc., 999 E. 46$^{th}$ St., Brooklyn, N.Y., 11203. Specifically, the preferred fragrance composition contains 3 parts Elias Fragrance Code No. 23238 to one part Elias Fragrance Code No. 211255. This fragrance composition is given by way of example. Other fragrances and fragrance compositions may also be used.

The foregoing written description relates to various embodiments of the present invention. Numerous changes and modifications may be made therein without departing from the spirit and scope of the invention as defined in the following claims.

What is claimed is:

1. An odor-eliminating air-freshener composition comprising a water-based deodorizing agent having semi-rigid, concave molecular structures which capture odor-causing molecules, soyaethyl morpholinium ethosulfate, and benzethonium chloride.

2. A composition according to claim 1, wherein the water-based deodorizing agent having semi-rigid, concave molecular structures which capture odor-causing molecules is present in an amount ranging from about 0.1% to about 5% by weight of the total composition.

3. A composition according to claim 1, wherein the soyaethyl morpholinium ethosulfate is present in an amount ranging from about 0.1% to about 5% by weight of the total composition.

4. A composition according to claim 1, wherein the benzethonium chloride is present in an amount ranging from about 0.1% to about 3% by weight of the total composition.

5. A composition according to claim 1, further comprising volatile and non-volatile solvents, solubilizing agents, chemical carriers, chelators, fragrances, and colorants.

6. A method for eliminating or neutralizing odor, comprising applying to a locus in need of such elimination or neutralization an air-freshening effective amount of a composition comprising a water-based deodorizing agent having semi-rigid, concave molecular structures which capture odor-causing molecules, soyaethyl morpholinium ethosulfate, and benzethonium chloride, wherein said application is performed by atomizing a liquid form of said composition at the locus in need of such elimination or neutralization.

7. The method according to claim 6, wherein the atomization is performed by a mechanical spraying device.

8. The method according to claim 6, wherein the atomization is performed by a compressed gas aerosol apparatus.

* * * * *